United States Patent
Gass et al.

(10) Patent No.: US 11,574,411 B2
(45) Date of Patent: Feb. 7, 2023

(54) DEFORMABLE IMAGE REGISTRATION BASED ON AN IMAGE MASK GENERATED BASED ON A TWO-DIMENSIONAL (2D) COMPUTED TOMOGRAPHY (CT) IMAGE

(71) Applicant: SIEMENS HEALTHINEERS INTERNATIONAL AG, Palo Alto, CA (US)

(72) Inventors: Tobias Gass, Vogelsang AG (CH); Thomas Schwere, Niederrohrdorf (CH); Marco Lessard, Trois-Rivieres (CA); Joerg Desteffani, Windisch (CH)

(73) Assignee: SIEMENS HEALTHINEERS INTERNATIONAL AG

( * ) Notice: Subject to any disclaimer, the term of this patent is extended or adjusted under 35 U.S.C. 154(b) by 0 days.

(21) Appl. No.: 17/156,575

(22) Filed: Jan. 23, 2021

(65) Prior Publication Data

US 2021/0142494 A1 May 13, 2021

Related U.S. Application Data

(63) Continuation of application No. 15/935,044, filed on Mar. 25, 2018, now Pat. No. 10,902,621.

(51) Int. Cl.
*G06T 7/33* (2017.01)
*G06T 7/11* (2017.01)
(Continued)

(52) U.S. Cl.
CPC .............. *G06T 7/337* (2017.01); *A61B 6/032* (2013.01); *A61B 6/4085* (2013.01);
(Continued)

(58) Field of Classification Search
None
See application file for complete search history.

(56) References Cited

U.S. PATENT DOCUMENTS

| 9,339,243 B2* | 5/2016 | Zhang | A61N 5/1049 |
| 10,388,036 B2* | 8/2019 | Chen | G06T 11/006 |

(Continued)

FOREIGN PATENT DOCUMENTS

| CN | 101743568 A | 6/2010 |
| CN | 107072595 A | 8/2017 |

(Continued)

OTHER PUBLICATIONS

The Extended European Search Report, Application No. 19162526.8, dated Jun. 18, 2019.

(Continued)

*Primary Examiner* — Tahmina N Ansari
(74) *Attorney, Agent, or Firm* — Su IP Consulting

(57) ABSTRACT

In accordance with at least some embodiments of the present disclosure, a process to improve computed tomography (CT) to cone beam computed tomography (CBCT) registration is disclosed. The process may include receiving a CT image generated by CT-scanning of an object, and receiving a CBCT image generated by CBCT-scanning of the object. The process may include generating an image mask based on Digital Imaging and Communications in Medicine (DICOM) information extracted from the CBCT image. For a specific pixel in the CBCT image, the image mask contains a corresponding data-field indicating whether the specific pixel contains image data generated based on the CBCT-scanning of the object. The process may further include generating a registered image by utilizing the image mask to perform a DIR between the CT image and the CBCT image.

20 Claims, 5 Drawing Sheets

(51) Int. Cl.
*G06T 7/149* (2017.01)
*A61B 6/03* (2006.01)
*G16H 30/20* (2018.01)
*A61B 6/00* (2006.01)
*G06T 5/00* (2006.01)
*G06T 7/30* (2017.01)

(52) U.S. Cl.
CPC ............ *A61B 6/5235* (2013.01); *G06T 5/004* (2013.01); *G06T 7/11* (2017.01); *G06T 7/149* (2017.01); *G06T 7/30* (2017.01); *G16H 30/20* (2018.01); *G06T 2207/10081* (2013.01)

(56) References Cited

U.S. PATENT DOCUMENTS

| | | | | |
|---|---|---|---|---|
| 10,485,988 | B2* | 11/2019 | Kuusela | A61N 5/103 |
| 2011/0280458 | A1* | 11/2011 | Flohr | G06T 11/008 |
| | | | | 382/131 |
| 2012/0263360 | A1* | 10/2012 | Zhu | G06T 11/005 |
| | | | | 382/131 |
| 2014/0073907 | A1* | 3/2014 | Kumar | A61B 34/10 |
| | | | | 600/407 |
| 2016/0371863 | A1* | 12/2016 | Simon | G06T 11/006 |
| 2017/0156690 | A1* | 6/2017 | Yi | A61B 6/5264 |
| 2018/0025510 | A1* | 1/2018 | Chen | A61B 6/4085 |
| | | | | 382/131 |
| 2018/0160933 | A1* | 6/2018 | Urman | G16H 50/50 |
| 2018/0185669 | A1* | 7/2018 | Kuusela | A61N 5/103 |
| 2019/0295268 | A1* | 9/2019 | Gass | A61B 6/5235 |

FOREIGN PATENT DOCUMENTS

| | | |
|---|---|---|
| CN | 107403446 A | 11/2017 |
| WO | 2016134127 A1 | 8/2016 |

OTHER PUBLICATIONS

L Archambault et al., "US-D-WAB-04: Restoration of CBCT Images by Deformable Registration for Plan Evaluation and Replanning", Fifth-fifth annul meeting of the American association of physicists in medicine, p. 107, Jun. 6, 2013, vol. 40, Issue 6, Part 3.

Xin Zhen et al., "Deformable Registration Between CT and Truncated CBCT for Adaptive Therapy Dose Calculation", Medical Physics, p. 3961, Jan. 1, 2012, vol. 39, No. 6.

Lin-Jing Wang et al., A GPU Based Improved Demons Algorithm for CT to CBCT Deformable Image Registration, Chinese Journal of Medical Physics, May 31, 2013, vol. 30, No. 3.

Xin Zhen et al., "Study of Deformabe Image Registration Between CT and Truncated CBCT Image", China Academic Journal Electronic Publishing House, Jun. 2014, vol. 33, No. 5.

Xin Li, Research on Key Techniques Relevant to Deformable Image Registration Algorithms in Adaptive Radiotherapy', Southern Medical University—Doctoral dissertation, 2017.

Shepeng Chen et al., "MR Image-based Synthetic CT for IMRT Prostate Treatment Planning and CBCT Image-guided Localization", Journal of Applied Clinical Medical Physics, 2016, vol. 17, No. 3.

* cited by examiner

DEFORMABLE IMAGE REGISTRATION BASED ON AN IMAGE MASK GENERATED BASED ON A TWO-DIMENSIONAL (2D) COMPUTED TOMOGRAPHY (CT) IMAGE

CROSS-REFERENCE TO RELATED APPLICATIONS

The present application is a continuation application under 35 U.S.C. § 120 of U.S. application Ser. No. 15/935,044 filed Mar. 25, 2018, now U.S. Pat. No. 10,902,621. The aforementioned U.S. application, including any appendices or attachments thereof, is hereby incorporated by reference in its entirety.

BACKGROUND

Unless otherwise indicated herein, the approaches described in this section are not prior art to the claims in this application and are not admitted to be prior art by inclusion in this section.

The deformable (non-rigid) image registration of a Computed Tomography (CT) image to a Cone Beam Computed Tomography (CBCT) image is an important operation in, for example, treatment planning, monitoring, and plan adaptation. The goal of the deformable image registration is to deform or warp one image to match another image as accurately as possible. In some situations, one image may contain a partial field of view of the scanning object, or with an image boundary that falsely resembles a skin-to-air interface. When performing automatic registration processing using this image and other images that contain the entire anatomy of a scanning object within the field of view of the image, the automatic registration processing may generate misleading cues and lead to wrong registration results. Such an outcome will have a substantial impact on the accuracy and reliability of automatized steps in treatment planning and monitoring.

DETAILED DESCRIPTION

Figure 1A:
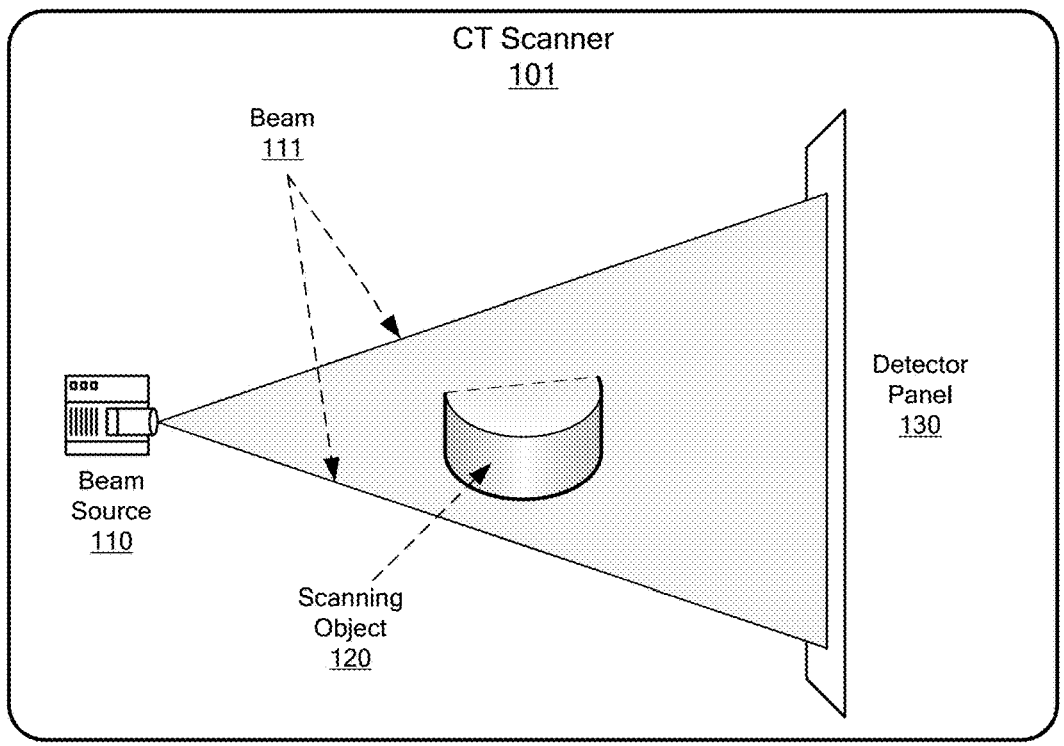
FIG. 1A shows a Computed Tomography (CT) scanner performing CT scanning operations.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated herein.

FIG. 1A shows a Computed Tomography (CT) scanner performing CT scanning operations, in accordance with certain embodiments of the present disclosure. Throughout the disclosure, the term "CT image" may broadly refer to a graphical image containing two-dimensional (2D) medical data generated from a single CT scanning operation. A "CT scanning operation" may include multiple "CT scanning interrogations" operating from multiple angles/directions, and may generate a set of corresponding CT projections. A CT reconstruction process may then generate one or more CT images based on this set of CT projections. Likewise, the term "CBCT image" may broadly refer to a graphical image containing 2D medical data generated from a single CBCT scanning operation, and a "CBCT scanning operation" may include multiple "CBCT scanning interrogations" operating from multiple angles/directions, and may generate a set of corresponding CBCT projections. A CBCT reconstruction process may then generate one or more CBCT images based on this set of CBCT projections.

In some embodiments, a CT scanner 101 may have, among other components, a beam source 110 and a detector panel 130. The beam source 110 may emit a beam 111 of particles (e.g., photons and/or electrons) toward a scanning object 120 (e.g., a patient) placed between the beam source 110 and the detector panel 130. The emitted particles may interact with the scanning object 120 through photo-electric absorptions, Rayleigh (or coherent) scattering, and Compton (or incoherent) scattering, and may or may not be detected by the detector panel 130 afterward.

In some embodiments, the detector panel 130 may be configured for sensing those particles passed through the scanning object 120 and/or reached the detector panel 130. The detector panel 130 may contain multiple pixels forming a long and narrow grid. Each pixel may detect the radioactive energy from the particles reaching the pixel, and the detector panel 130 may utilize the deposited energies detected by all the pixels to generate one or more CT projections. In some cases, the detector panel 130 may be flat (as shown in FIG. 1A), or may have an arc shape.

In some embodiments, during a single CT scanning interrogation, the beam source 110 may project particles towards the detector panel 130 at a particular angle/direction, and the CT scanner 101 may generate a single CT projection, based on the particles detected by the detector panel 130. Each CT projection may contain 2D image data illustrating the cross-sectional internal structure of the scanning object 120 from the particular angle/direction. Afterward, the beam source-detector panel (source-detector pair) may be rotated to a different angle/direction to perform another round of CT scanning interrogation of the scanning object 120, for the CT scanner 101 to generate another CT projection.

In some embodiments, the particles projected from the beam source 110 may form a fan-shaped beam (fan beam) having a narrow beam-width in one dimension and a wider beam-width in the other dimension. A CT scanning operation may include the source-detector pair rotating and traveling in a helix/spiral fashion to traverse the whole scanning object 120 and generating a set of CT projections. The set of CT projections may be used in a subsequent reconstruction process to generate one or more CT images.

Figure 1B:
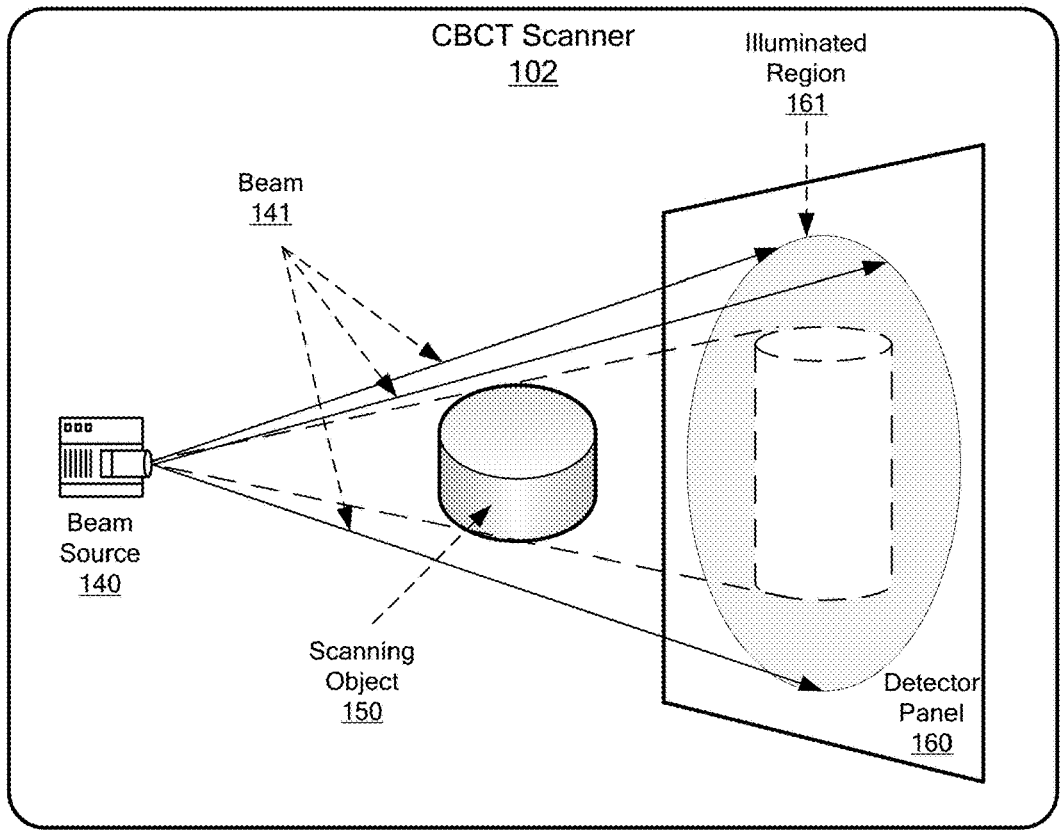
FIG. 1B shows a Cone Beam Computed Tomography (CBCT) scanner performing CBCT scanning operations.

FIG. 1B shows a Cone Beam Computed Tomography (CBCT) scanner performing CBCT scanning operations, in accordance with certain embodiments of the present disclosure. Similar to the CT scanner 101 of FIG. 1A, the CBCT scanner 102 may have, among other components, a beam source 140 and a detector panel 160. The beam source 140 may emit a beam 141 of particles toward a scanning object 150 (e.g., a patient) placed between the beam source 140 and the detector panel 160. The beam source 140 and the detector panel 160 may be fixated on a gantry which rotates around the scanning object 150 positioned near its middle. The detector panel 160 may be configured for sensing those particles passed through the scanning object 150 and/or reached the detector panel 160. The detector panel 160 may contain multiple particle-sensing pixels forming a substantially square grid, and may utilize the deposited energies detected by the pixels to generate a CBCT projection.

In some embodiments, during a single CBCT scanning interrogation, the beam source 140 may project particles towards the detector panel 160 in a particular angle/direction, and the CBCT scanner 102 may generate a single CBCT projection based on the particles detected by the detector panel 160. Each CBCT projection may contain 2D image data representing the internal structure of the scanning object 150 from the particular angle/direction. Afterward, the beam source-detector panel (source-detector pair) may be rotated to a different angle/direction to perform another round of CBCT scanning interrogation of the scanning object 150, thereby allowing the CBCT scanner 102 to generate another CBCT projection. The CBCT scanner 102 may control the source-detector pair to rotate around the scanning object 150 in one circle, and generate a set of multiple sequential, planar CBCT projections. The set of CBCT projections may be used in a subsequent reconstruction process to generate one or more CBCT images.

In some embodiments, as shown in FIG. 1B, the particles emitted from the beam source 140 may form a pyramidal-shaped or cone-shaped beam (conical beam) which covers the entire scanning object 150 (or covers the entire area-of-interest of the scanning object 150). Specifically, the beam 141 may lead to the generating of a planar projection on the detector panel 160 with a field of view (FOV) of the whole scanning object 150. In other words, each CBCT projection generated by the CBCT scanner 102 may incorporate the entire FOV of the scanning object 150, while each CT projection generated by the CT scanner 101 may only show a slice of the FOV.

In some embodiments, during a CBCT scanning interrogation, a conical beam of the CBCT scanner 102 may form a substantially-circular illuminated region 161 on the detector panel 160, as the particles emitted from the beam source 140 may be within the boundary of the conical beam and may mostly reach those pixels of the detector panel 160 that are within the illuminated region 161. In other words, the pixels of the detector panel 160 that are outside of the illuminated region 161 may either not detect any particles generated by the beam source 140, or may detect those particles that are reflected or scattered by the scanning object 150. Thus, the CBCT scanner 102 may generate a CBCT projection that also has such an illuminated region, and any image data that are inside of this illuminated region in the CBCT projection may be deemed meaningful and valid, and any image data outside of this illuminated region in the CBCT projection may be deemed void, incidental, meaningless, or unreliable.

In some embodiments, the illuminated region 161 may also be related to the size of the detector panel 160 utilized by the CBCT scanner 102. In other words, the detector panel 160 is not large enough to cover the whole illuminated region 161, thereby indirectly resulting in a limited FOV for the CBCT projections generated by the CBCT scanner 102. In this case, the CBCT projection may seem to have a somewhat limited "illuminated region," as some of the image data that are outside of the coverage of the detector panel 160 may also be void and meaningless.

In some embodiments, one approach to generate a CT image may algorithmically reconstruct a three-dimensional (3D) volume of the scanning object 120 from multiple CT projections obtained via a helical progression, and CT images may be generated by "slicing" through this 3D volume. Alternatively, another reconstruction process may include back-projecting multiple CT projections to generate a corresponding CT image. Likewise, multiple CBCT projections obtained via one rotational sequence of the CBCT gantry may go through similar image reconstruction processes to generate one or more CBCT images. Regardless of the reconstruction processes, the generated CT images and/or CBCT images may always be affected by factors such as whole-or-partial FOV and illuminated regions that are inherent in the CT projections and CBCT projections.

In some embodiments, the scanning object 120 may be subjected to a higher amount of radiation exposure during a CT scanning operation than during a CBCT scanning operation. Specifically, the CBCT scanner 102 may have a quicker rotation motion compared to the spiral motion of the CT scanner 101, leading to lower doses of radiation during a CBCT scanning operation. Further, in a CT scanning operation, a patient may need to lie down on a scanning table, while a CBCT scanning operation may allow the patient to stand freely within the CBCT scanner's gantry. Thus, when a CT scanning operation and a CBCT scanning operation are performed on the same scanning object, the CT images and CBCT images may need to be registered under a common coordination system.

Figure 2:
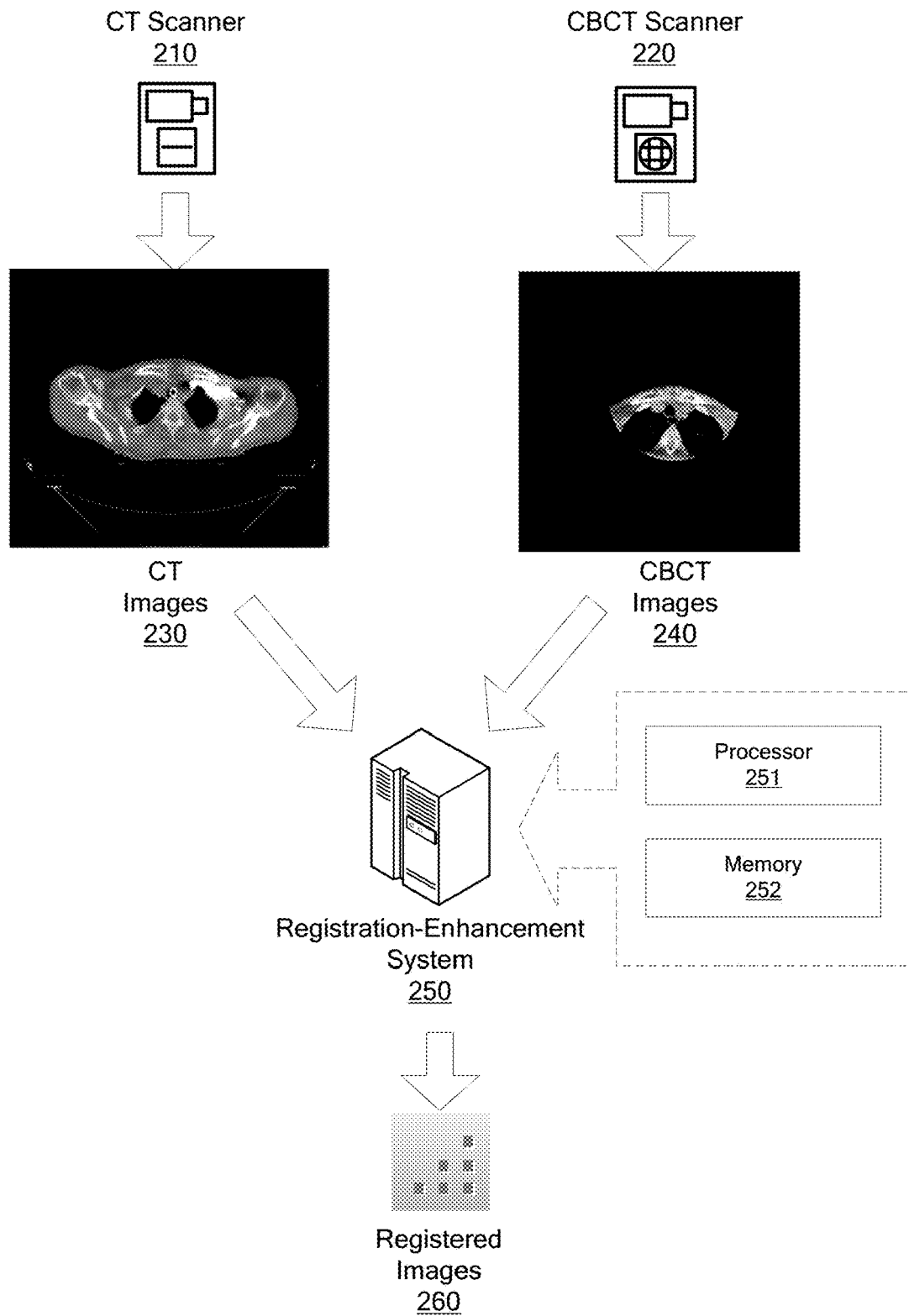
FIG. 2 shows a block diagram illustrating an exemplary system configured to improve CT to CBCT registration.

FIG. 2 shows a block diagram illustrating an exemplary system configured to improve CT to CBCT registration, in accordance with certain embodiments of the present disclosure. In FIG. 2, a CT scanner 210 may perform a CT scanning operation on an object (e.g., a patient), and generate a set of CT Images 230, and a CBCT scanner 220 may perform a CBCT scan operation on the same object to generate a set of CBCT images 240. A registration-enhancement system 250 may take the CT images 230 and CBCT images 240 as inputs, perform a Deformable Image Registration (DIR) operation based on the CT images 230 and the CBCT images 240, and generate a set of registered images 260 that have enhanced quality. The registered images 260 may be used to for diagnostic purposes and medical treatments including dose accumulation, contour propagation, mathematical modeling, automatic segmentation, and functional imaging.

In some embodiments, the registration-enhancement system 250 may be configured to perform an enhanced Deformable Image Registration (DIR) operation based on the CT images 230 and the CBCT images 240, and generated one or more registered images 260. "Image registration" or "registration" may refer to a process of transforming different sets of data into one coordinate system. DIR may refer to a process to locally register one image data set into a reference image set. In other words, DIR is a process of finding a point-to-point spatial correspondence between two or among multiple sets of images, and finding a mapping between positions in one image and the positions in another image. For example, the DIR process may find the geometric correspondence between the multiple sets of images that differ in time, space, modality, and even subject.

In some embodiments, the registration-enhancement system 250 may perform the DIR to map one of the CT images 230 with a corresponding one of the CBCT image 240, and generate one corresponding registered image 260 that contains multiple deformation vector fields (DVFs) defining the motions of each image pixel (or image voxel) from the CT image 230 to the CBCT image 240. Alternatively, the registration-enhancement system 250 may perform a reverse DIR to map one of the CBCT images 240 with a corresponding one of the CT image 230, and generate a corresponding registered image 260 that contains DVFs defining the motions of each image pixel (or image voxel) from the CBCT image 240 to the CB image 230.

In some embodiments, when performing a DIR to map a CT image to a CBCT image, the registration-enhancement system 250 may misidentify the image data that is outside of the illuminated region of the CBCT image as meaningful image data associated with water or air, or misinterpret the boundary of the illuminated region of the CBCT image as a skin-to-air boundary. Such misidentification or misinterpretation may lead to the generating of a mis-coordinated registered image. In some embodiments, the registration-enhancement system 250 may perform the enhanced DIR process to reduce or eliminated the potential misidentification or misinterpretation due to the restricted illuminated region in the CBCT image.

In some embodiments, the registration-enhancement system 250 may include one or more processors 251, memory 252, and/or other components, so that it could perform the enhanced DIR operation based on the CT images 230 and the CBCT images 240. The processor(s) 251 may include central processing units (CPUs) for controlling the overall operation of the registration-enhancement system 250. The processor(s) 251 may accomplish this by executing software or firmware stored in memory 252. The processor(s) 251 may be or may include, one or more programmable general-purpose or special-purpose microprocessors, digital signal processors (DSPs), programmable controllers, application specific integrated circuits (ASICs), programmable logic devices (PLDs), graphical processing units (GPUs) or the like, or a combination of such devices. The memory 252 may represent any form of random access memory (RAM), read-only memory (ROM), flash memory (as discussed above), or the like, or a combination of such devices. In use, the memory 252 may contain, among other things, a set of non-transitory machine-readable instructions which, when executed by the processor 251, causing the processor 251 to perform at least some embodiments of the present disclosure.

Figure 3:
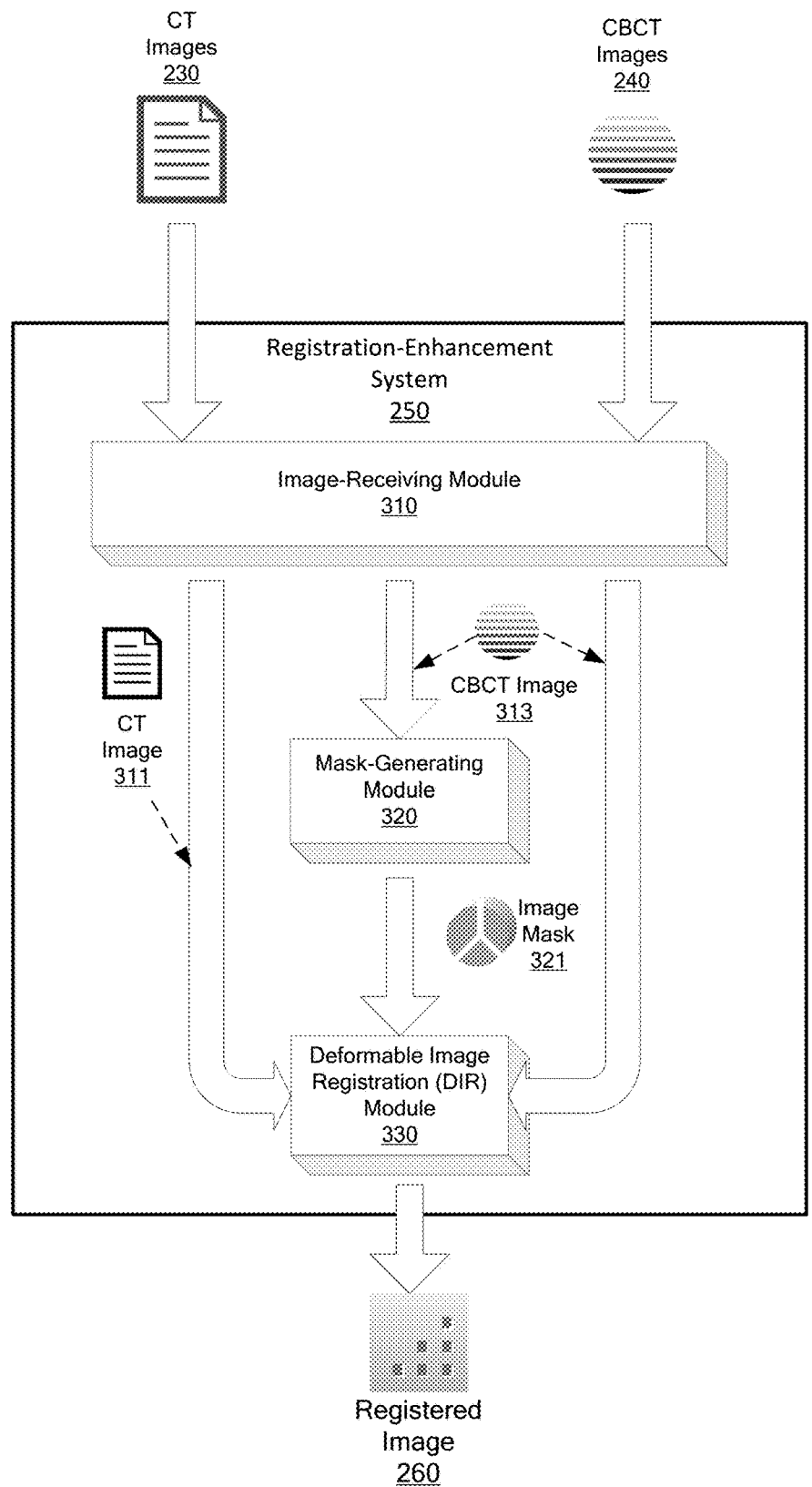
FIG. 3 illustrates details of a registration-enhancement system for improving CT to CBCT registration.

FIG. 3 illustrates details of a registration-enhancement system for improving CT to CBCT registration, in accordance with certain embodiments of the present disclosure. In FIG. 3, the registration-enhancement system 250 may be configured to perform an enhanced DIR operation on the CT images 230 and the CBCT images 240. The registration-enhancement system 250 may contain, among other elements, an image-receiving module 310, a mask-generating module 320, and a DIR module 330. The modules contained in the registration-enhancement system 250 may be implemented either as hardware components or software applications running on a suitable computer. Further, some of the above modules may be combined into a single module, or a single module may be divided into additional sub-modules not shown in FIG. 3. For convenience purposes, the CT images 230, CBCT images 240, registration-enhancement system 250, and the registered image 260 correspond to their respective counterparts in FIG. 2.

In some embodiments, the image-receiving module 310 of the registration-enhancement system 250 may be configured to receive a set of CT images 230 and a corresponding set of CBCT images 240. The CT images 230 and the CBCT images 240 may be generated based on a common object (e.g., the same patient). Specifically, each one of the CT images 230 may be associated with one or more of the CBCT images 240. In other words, each one of the CT images 230 may contain image data corresponding to body regions and organs, and such image data may match or supplement image data contained in one or more of the CBCT images 240 that corresponding to the same body regions and organs. Likewise, each of the CBCT images 240 may be associated with one or more of the CT images 230.

In some embodiments, the image-receiving module 310 may select a specific CT image 311 from the CT images 230, and a specific CBCT image 313 from the CBCT images 240 for DIR processing. In some situations, even though associated with the same scanning object, the CT image 311 typically contains the entire anatomy within the field-of-view of the CT scanner, the CBCT image 313 may contain a number of pixels that are limited by the cylindrical volume of the CBCT scanner. The image-receiving module 310 may transfer the CBCT image 313 to the mask-generating module 320 for generating an image mask 321 based on the CBCT image 313. Afterward, the image-receiving module 310 may transmit the CT image 311 and the CBCT image 313 to the DIR module 330, and the mask-generating module 320 may concurrently transmit the image mask 321 to the DIR module 330. The DIR module 330 may then generate a corresponding registered image 260 by performing an enhanced DIR operation based on the CT image 311, the CBCT image 313, and the image mask 321 that is generated based on the CBCT image 313.

Figure 4:
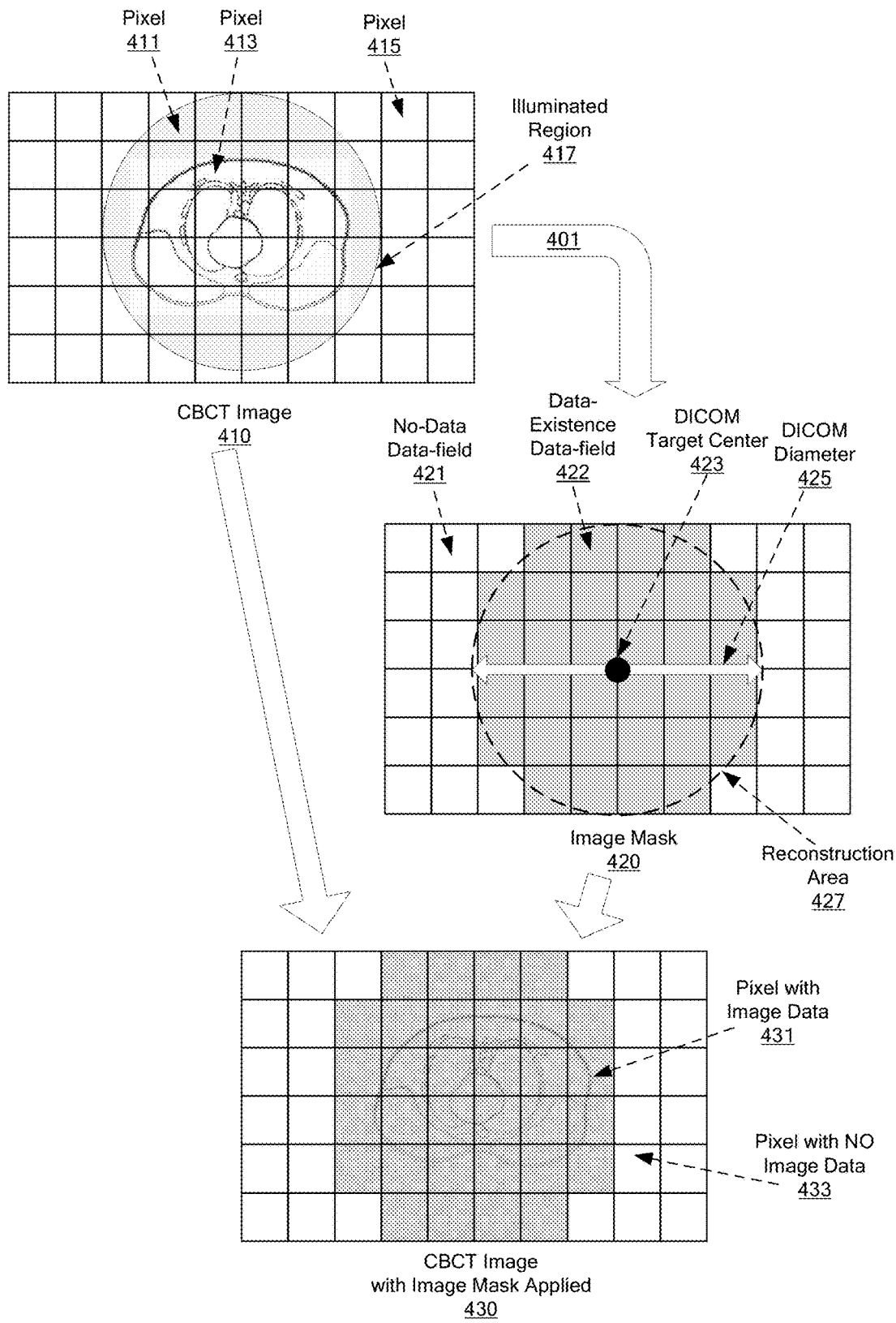
FIG. 4 illustrates an example scenario to construct and utilize an image mask during an enhanced Deformable Image Registration (DIR) operation.

FIG. 4 illustrates an example scenario to construct and utilize an image mask during an enhanced DIR operation, in accordance with certain embodiments of the present disclosure. In FIG. 4, a registration-enhancement system (similar to the registration-enhancement 250 of FIG. 2) may first generate (401) an image mask 420 based on a CBCT image 410. Afterward, the registration-enhancement system may apply the image mask 420 on the CBCT image 410 to generate an output that can be illustrated by the CBCT image with-image-mask-applied 430.

In some embodiments, the CBCT image 410 may contain a 2D set of pixels. Each "pixel" may contain a value in a 2D space representing graphical information such as a Hounsfield Units (HU) value. As shown in FIG. 4, the CBCT Image 410 may include pixels such as pixels 411, 413, and 415. In some embodiments, the CBCT Image 410 may have an illuminated region 417 that is located within the cylindrical volume of the CBCT conical beam. In this case, the pixels that are within this illuminated region 417 may contain actual image data, while pixels that are outside of this illuminated region 417 may contain meaningless image data. For example, the pixel 413 is within the illuminated region 417, and therefore contains real image data generated based on the particles passing through a scanning object. Pixel 415 is outside of the illuminated region 417, and has meaningless value. In comparison, pixel 411 may be at or near the boundary of the cylindrical volume but within the illuminated region 417. Even though pixel 411 may be outside of the scanning object and contain data that represents air or water, it should nevertheless be treated as containing valid image data.

In some embodiments, the registration-enhancement system may generate an image mask 420 based on the CBCT Image 410. The "image mask" may contain a set of data-fields having one-to-one correspondences to the set of pixels in the CBCT image 410. Specifically, each "data-field" in the image mask 420 may be associated with a specific pixel in the CBCT image 410, and may store various information related to this associated pixel. For example, each data-field in the image mask 420 may store a value indicating whether the associated pixel in the CBCT image 410 contains meaningful data or not. In other words, if the data-field contains a "no-data" value, it may mean that the associated pixel does not contain any image data, or that any image data contained in the associated pixel are meaningless and should be ignored. Likewise, if the data-field contains a "data-existence" value, it may mean that the associated pixel contains image data, or that the image data contained in the associated pixel, even if equalling to zeros or null, should be treated as valid and meaningful value. In FIG. 4's example, data-field 421 may be a data-field that contains a "no-data" value, and data-field 422 may be a data-field that contains a "data-existence" value.

In some embodiments, the registration-enhancement system may automatically generate the image mask 420 based on Digital Imaging and Communications in Medicine (DICOM) information stored in the CBCT images 410. Specifically, the registration-enhancement system may extract, from one or more of the CBCT images 410, DICOM information such as "DICOM Reconstruction Target Center" and "DICOM Reconstruction Diameter." The DICOM Reconstruction Target Center 423 may refer to the center location of the circular illuminated region formed during a CBCT scanning operation. The DICOM Reconstruction Diameter 425 may refer to the diameter of such illuminated region.

In some embodiments, based on the DICOM information extracted from the CBCT image 410, the registration-enhancement system may generate a circular reconstruction area 427, by having the DICOM target center 423 as the circle's center and the DICOM diameter 425 as the circle's diameter. The reconstruction area 427 may correspond to the illuminated region 417 of the CBCT image 410, as the reconstruction area 427 may have substantially the same size and location in the image mask 420 as the size and location of the illuminated region 417 in the CBCT image 410. In other words, the reconstruction area 427 may simulate and recreate the effect of the illuminated region 417 on the CBCT scanner's detector panel during a CBCT scanning operation, as well as simulate the distribution of the meaningful image data in the CBCT image 410.

In some embodiments, the registration-enhancement system may then apply the circular reconstruction area 427 to the 2D data-fields as shown in FIG. 4. Afterward, any data-fields in the image mask 420 that are covered by, or within the boundary of, the reconstruction area 427 may be deemed having meaningful image data, and may be assigned with a "data-existence" value. In comparison, any data-fields in the image mask 420 that are not covered by, or outside the boundary of, the reconstruction area 427 may be deemed to have meaningless image data, and may be assigned a "no-data" value. Thus, the registration-enhancement system may assign either "no-data" value or "data-existence" value to each of the data-fields in the image mask 420 by evaluating the data-fields' relative positions with respect to the reconstruction area 427 in the image mask 420. For illustrational purpose, in FIG. 4, those data-fields that have "data-existence" values are filled with grey colors, and those data-fields that have "no-data" values are filled with white colors.

In some embodiments, the registration-enhancement system may further include a specific material type and density value in each of the data-fields in the image mask 420, based on the HU values of the pixels in the CBCT image 410. A data-field's material type and density value may determine the associated pixel's x-ray attenuation and scattering properties. Exemplary material types may include, without limitation, air, water, bone, adipose, lung, muscle, and cartilage. A data-field's density value may then be determined based on the associated pixel's material type, according to the material type's physical characteristics.

In some embodiments, each of the multiple CBCT images 410 that are generated during a single CBCT scanning operation may contain the same DICOM Reconstruction Target Center and DICOM Reconstruction Diameter information. In this case, the registration-enhancement system may generate one image mask 420 based on any one of the multiple CBCT images 410, and apply this one image mask 420 to all of the CBCT images 410. Alternatively, the multiple CBCT images 410 that are generated during one or more CBCT scanning operations may contain different DICOM information. In this situation, the registration-enhancement system may generate a specific image mask 420 for each of the CBCT images 410, and apply the specific image mask 420 to the corresponding CBCT image 410.

In some embodiments, after the image mask 420 is generated based on a CBCT image 410, the registration-enhancement system may utilize the image mask 420 during a DIR operation between a CT image and the CBCT image 410. Specifically, when performing registration of a specific pixel in the CBCT image 410, the registration-enhancement system may extract from the image mask 420 the data-field that is associated with the specific pixel, and evaluate the data contained therein. If the associated data-field contains "no-data" (as shown by data-field 421), the registration-enhancement system may bypass or ignore the specific pixel of the CBCT image 410 in the DIR operation. Alternatively, if the associated data-field contains "data-existence" (as shown by data-field 422), the registration-enhancement system may further process the specific pixel of the CBCT image 410 in the subsequent DIR operation.

In some embodiments, the outcome of utilizing the image mask during a DIR operation as described above may be shown by a CBCT image with image mask applied 430 in FIG. 4. For example, during the DIR operation, the registration-enhancement system may quickly identify pixel 431 as a pixel with image data, and determine that pixel 433 may be a pixel with no image data (or with meaningless image data). In this approach, the registration-enhancement system may improve the DIR operation by ignoring and eliminating the processing of any pixels that contain no image data.

In some embodiments, when the data-field contains additional information such as material type and density value, the registration-enhancement system may utilize such additional information to better determine the correspondence between the CT image and the CBCT image. Specifically, when a pixel is deemed to have image data, the registration-enhancement system may retrieve additional information from the data-field associated with the pixel, and utilize the additional information to further improve the DIR operation between the CT image and CBCT image.

In some embodiments, the registration-enhancement system may also utilize the same enhancement process as described above to process a CT volume which contains a set of three-dimensional (3D) cells (or "voxels"). A voxel represents a value on a fixed and regular grid in 3D space, and may correspond to one of the multiple 3D structures, such as, without limitation, cubes, rectangular cuboids, hexagonal structures, or structures in any isotropic/non-isotropic shapes and sizes (e.g., 1 cm). In this case, the registration-enhancement system may reconstruct a CT volume based on a set of CT images, and reconstruct a CBCT volume based on a set of CBCT images. Afterward, the registration-enhancement system may generate a 3D image mask that contains 3D data-fields having one-to-one associations with the voxels in the CBCT volume. The 3D data-fields may be used to indicate whether the corresponding voxels in the CBCT volume has "no-data" or "data-existence" value, according to the DICOM information in the CBCT images. The registration-enhancement system may then utilize the 3D image mask for the DIR processing between the CT volume and CBCT volume.

In some embodiments, the above-described technique may also be applicable for registrations between 3D images of any modality, as long as one 3D image is reconstructed from 2D projections that includes a similar "illuminated region" as illustrated above. In other words, the registration-enhancement system may generate a 3D image mask for the 3D image having the illuminated region, and utilize the 3D image mask for the DIR processing between the 3D images without illuminated region and the 3D image with illuminated region. Further, the above-described technique may also be applicable to registration from a MR image to a CBCT/CT image.

In some embodiments, the registration-enhancement system may utilize additional DICOM information embedded in the CBCT images to generate a non-circular image mask. Specifically, the registration-enhancement system may extract DICOM information related to patient-based coordinate system or utilize other processing means, in order to better determine the shape of the scanning object in the CBCT image. Afterward, the registration-enhancement system may generate the non-circular image mask that can further enhance the accuracy of the DIR processing.

Figure 5:
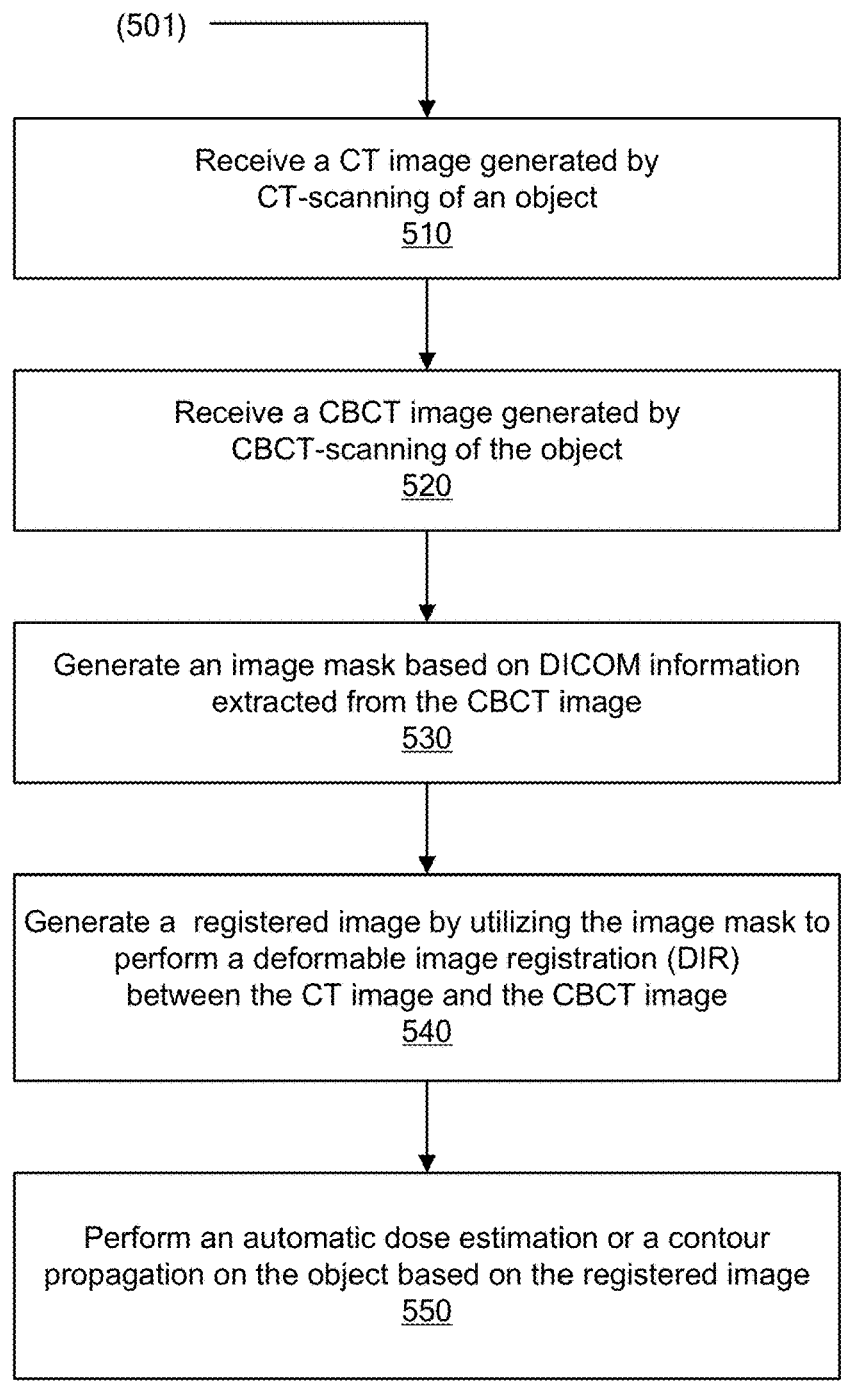
FIG. 5 shows a flow diagram illustrating one embodiment of a process to improve CT to CBCT registration, all in accordance with certain embodiments of the present disclosure.

FIG. 5 shows a flow diagram illustrating one embodiment of a process 501 to improve CT to CBCT registration, in accordance with certain embodiments of the present disclosure. The process 501 sets forth various functional blocks or actions that may be described as processing steps, functional operations, events, and/or acts, which may be performed by hardware, software, and/or firmware. Those skilled in the art in light of the present disclosure will recognize that numerous alternatives to the functional blocks shown in FIG. 5 may be practiced in various implementations. In some embodiments, machine-executable instructions for the process 501 may be stored in memory, executed by a processing unit, and/or implemented in a registration-enhancement system, such as the registration-enhancement system 250 of FIG. 2.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments. Moreover, one or more of the outlined steps and operations may be performed in parallel.

At block 510, a registration-enhancement system, which may be configured to improve computed tomography (CT) to cone beam computed tomography (CBCT) registration, may receive a CT image generated by CT-scanning of an object. The object may be a patient or an area-of-interest of a patient.

At block 520, the registration-enhancement system may receive a CBCT image generated by CBCT-scanning of the same object.

At block 530, the registration-enhancement system may generate an image mask based on Digital Imaging and Communications in Medicine (DICOM) information extracted from the CBCT image. In some embodiments, the DICOM information may include at least DICOM Target Center and DICOM Reconstruction Diameter.

In some embodiments, for a specific pixel in the CBCT image, the image mask contains a corresponding data-field indicating whether the specific pixel contains image data generated based on the CBCT-scanning of the object. In other words, if the image data contained in the specific pixel is not generated by particles within a conical beam emitting from the CBCT scanner's beam source, or if the specific pixel is outside of an illuminated region formed on the CBCT scanner's detector panel, then the image data may be deemed not generated based on the CBCT-scanning of the object. Otherwise, the image data may be deemed generated based on the CBCT-scanning of the object.

In some embodiments, the registration-enhancement system may construct a reconstruction area for the CBCT image based on the DICOM Target Center and DICOM Reconstruction Diameter extracted from the CBCT image. Specifically, the reconstruction area for the CBCT image may correspond to the illuminated region formed on the CBCT scanner's detector panel and manifested in the CBCT image.

In some embodiments, upon a determination that the specific pixel is outside the reconstruction area for the CBCT image, the registration-enhancement system may assign a no-data value to the corresponding data-field in the image mask that is associated with the specific pixel. Alternatively, upon a determination that the specific pixel is inside the reconstruction area for the CBCT image, the registration-enhancement system may assign a data-existence value to the corresponding data-field in the image mask that is associated with the specific pixel.

At block 540, the registration-enhancement system may generate a registered image by utilizing the image mask to perform a DIR between the CT image and the CBCT image. Specifically, the registration-enhancement system may select a first pixel from the CBCT image and a second pixel from the CT image. The registration-enhancement system may then extract from the image mask a first data-field associated with the first pixel. Upon a determination that the first data-field contains a data-existence value, the registration-enhancement system may use the first pixel during the performing of the DIR.

In some embodiments, the registration-enhancement system may further select a third pixel from the CBCT image and a fourth pixel from the CT image. The registration-enhancement system may then extract from the image mask a second data-field associated with the third pixel. Upon a determination that the second data-field contains a no-data value, the registration-enhancement system may ignore or skip the third pixel during the performing of the DIR.

At block 550, the registration-enhancement system may then perform an automatic dose estimation or a contour propagation on the object based on the registered image. Alternatively, the registration-enhancement system may transmit the registered image to any third-party system for further processing, such as automatic image segmentation, organ and tumor localization, volume calculations, and patient positioning.

In some embodiments, organ motion that occurs during a CT and a CBCT scanning operation may lead to uncertainties in dose deliveries to the tumor and the organs at risk. Typical motion patterns may include volume and shape changes. In this case, the registration-enhancement system may perform the above-mentioned enhanced DIR operation to generate registered images, which can be used to perform dose accumulation and contour propagation for the tumor and the organs at risk. Specifically, the registration-enhancement system may utilize the registered image to better propagate the contours of the tumor and organs determined from the CT images onto the corresponding CBCT images. Likewise, the registration-enhancement system may utilize the registered image to better identify regions and areas of the tumor and organs in the CT image and CBCT images, thereby allowing a better estimation of the radioactive dosages these tumor and organs may encounter during the CT and CBCT scanning operation.

Thus, methods and systems for improving CT to CBCT registration have been described. The techniques introduced above can be implemented in special-purpose hardwired circuitry, in software and/or firmware in conjunction with programmable circuitry, or in a combination thereof. Special-purpose hardwired circuitry may be in the form of, for example, one or more application-specific integrated circuits (ASICs), programmable logic devices (PLDs), field-programmable gate arrays (FPGAs), and others.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. Those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

Software and/or firmware to implement the techniques introduced here may be stored on a non-transitory machine-readable storage medium and may be executed by one or more general-purpose or special-purpose programmable microprocessors. A "machine-readable storage medium", as the term is used herein, includes any mechanism that provides (i.e., stores and/or transmits) information in a form accessible by a machine (e.g., a computer, network device, personal digital assistant (PDA), mobile device, manufacturing tool, any device with a set of one or more processors, etc.). For example, a machine-accessible storage medium includes recordable/non-recordable media (e.g., read-only memory (ROM), random access memory (RAM), magnetic disk storage media, optical storage media, flash memory devices, etc.)

Although the present disclosure has been described with reference to specific exemplary embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense.

We claim:

1. A method, comprising:
   receiving a two-dimensional (2D) computed tomography (CT) image of an object;
   receiving a 2D cone beam computed tomography (CBCT) image of the object;
   generating an image mask based on the 2D CBCT image, wherein:
      for a specific first pixel in the 2D CBCT image, the image mask contains a corresponding first data-field indicating that the specific first pixel contains valid image data that are generated based on CBCT-scanning of the object, and
      for a specific second pixel in the 2D CBCT image, the image mask contains a corresponding second data-field indicating that the specific second pixel contains invalid image data or no image data that are generated based on CBCT-scanning of the object; and
   performing a deformable image registration (DIR) operation to generate a registered image based on the image mask, the 2D CT image, and the 2D CBCT image.

2. The method as recited in claim 1, further comprising:
   performing a dose estimation or a contour propagation on the object based on the registered image.

3. The method as recited in claim 1, further comprising:
   extracting information associated with an illuminated region from the 2D CBCT image.

4. The method as recited in claim 3, wherein the generating of the image mask further comprises:
   generating a reconstruction area for the 2D CBCT image based on the information associated with the illuminated region; and
   assigning a data value to the corresponding first data-field in the image mask that is associated with the specific first pixel based on a determination that the specific first pixel is within a boundary of the reconstruction area for the 2D CBCT image.

5. The method as recited in claim 3, wherein the information associated with the illuminated region includes Digital Imaging and Communications in Medicine (DICOM) Reconstruction Target Center, DICOM Reconstruction Diameter, or DICOM Reconstruction Target Center and DICOM Reconstruction Diameter.

6. The method as recited in claim 4, wherein the generating of the image mask further comprises:
   assigning a material type and density value associated with the specific first pixel to the corresponding first data-field in the image mask based on a Hounsfield Units (HU) value of the specific first pixel.

7. The method as recited in claim 1, wherein the generating of the registered image further comprises:
   selecting the first pixel from the 2D CBCT image and the second pixel from the 2D CT image;
   extracting from the image mask the first data-field associated with the first pixel, and the second data-field associated with the second pixel; and
   determining to use the first pixel to perform the DIR operation based on a data value assigned to the first data-field, and determining to bypass the second pixel for the DIR operation based on a data value assigned to the second data-field.

8. A method, comprising:
receiving a plurality of two-dimensional (2D) computed tomography (CT) images of an object;
receiving a plurality of 2D cone beam computed tomography (CBCT) images of the object;
generating an image mask based on a specific 2D CBCT image selected from the 2D CBCT images, wherein:
for a specific first pixel in the specific 2D CBCT image, the image mask contains a corresponding first data-field indicating that the specific first pixel contains valid image data that are generated based on CBCT-scanning of the object, and
for a specific second pixel in the 2D CBCT image, the image mask contains a corresponding second data-field indicating that the specific second pixel contains invalid image data or no image data that are generated based on CBCT-scanning of the object; and
performing a deformable image registration (DIR) operation to generate one of a plurality registered images based on the image mask, one of the plurality of 2D CT images, and the specific 2D CBCT image.

9. The method as recited in claim 8, further comprising:
extracting information associated with an illuminated region from the specific 2D CBCT image.

10. The method as recited in claim 9, wherein the generating of the image mask further comprises:
generating a reconstruction area for the specific 2D CBCT image based on the information associated with the illuminated region; and
assigning a data value to the corresponding first data-field in the image mask that is associated with the specific first pixel based on a determination that the specific first pixel is within a boundary of the reconstruction area for the specific 2D CBCT image.

11. The method as recited in claim 10, wherein the information associated with the illuminated region includes Digital Imaging and Communications in Medicine (DICOM) Reconstruction Target Center, DICOM Reconstruction Diameter, or DICOM Reconstruction Target Center and DICOM Reconstruction Diameter.

12. The method as recited in claim 11, wherein the information associated with the illuminated region extracted from each of the plurality of 2D CBCT images includes identical DICOM Target Center and DICOM Reconstruction Diameter.

13. The method as recited in claim 11, wherein the generating of the image mask further comprises:
assigning a material type and density value associated with the specific first pixel to the corresponding first data-field in the image mask based on a Hounsfield Units (HU) value of the specific first pixel.

14. The method as recited in claim 8, wherein the generating of the registered image further comprises:
selecting the first pixel from the 2D CBCT image and the second pixel from the 2D CT image;
extracting from the image mask the first data-field associated with the first pixel, and the second data-field associated with the second pixel; and
determining to use the first pixel to perform the DIR operation based on a data value assigned to the first data-field, and determining to bypass the second pixel for the DIR operation based on a data value assigned to the second data-field.

15. A registration-enhancement system, comprising:
a processor; and
a non-transitory computer-readable medium having stored thereon instructions that, in response to execution by the processor, cause the system to:
receive a two-dimensional (2D) computed tomography (CT) image of an object;
receive a 2D cone beam computed tomography (CBCT) image of the object;
generate an image mask based on the 2D CBCT image, wherein:
for a specific first pixel in the 2D CBCT image, the image mask contains a corresponding first data-field indicating that the specific first pixel contains valid image data that are generated based on CBCT-scanning of the object, and
for a specific second pixel in the 2D CBCT image, the image mask contains a corresponding second data-field indicating that the specific second pixel contains invalid image data or no image data that are generated based on CBCT-scanning of the object; and
perform a deformable image registration (DIR) operation to generate a registered image based on the image mask, the 2D CT image, and the 2D CBCT image.

16. The registration-enhancement system of claim 15, wherein the non-transitory computer-readable medium has stored thereon additional instructions that, in response to execution by the processor, cause the system to:
extract information associated with an illuminated region from the 2D CBCT image.

17. The registration-enhancement system of claim 16, wherein the instructions that cause the system to generate the image mask further cause the system to:
generate a reconstruction area for the 2D CBCT image based on the information associated with the illuminated region; and
assign a data value to the corresponding first data-field in the image mask that is associated with the specific first pixel based on a determination that the specific first pixel is within a boundary of the reconstruction area for the 2D CBCT image.

18. The registration-enhancement system of claim 16, wherein the information associated with the illuminated region includes Digital Imaging and Communications in Medicine (DICOM) Reconstruction Target Center, DICOM Reconstruction Diameter, or DICOM Reconstruction Target Center and DICOM Reconstruction Diameter.

19. The registration-enhancement system of claim 17, the instructions that cause the system to generate the image mask further cause the system to:
assign a material type and density value associated with the specific first pixel to the corresponding data-field in the image mask based on a Hounsfield Units (HU) value of the specific first pixel.

20. The registration-enhancement system of claim 15, wherein the instructions that cause the system to generate the image mask further cause the system to:
select the first pixel from the 2D CBCT image and the second pixel from the 2D CT image;
extract from the image mask the first data-field associated with the first pixel, and the second data-field associated with the second pixel; and determine to use the first pixel to perform the DIR operation based on a data value assigned to the first data-field, and determine to bypass the second pixel for the DIR operation based on a data value assigned to the second data-field.

* * * * *